(12) United States Patent
Urtel et al.

(10) Patent No.: US 7,507,866 B2
(45) Date of Patent: Mar. 24, 2009

(54) METHOD FOR PRODUCING OPTICALLY ACTIVE ALCOHOLS OR CARBOXYLIC ACIDS

(75) Inventors: Heiko Urtel, Edingen-Neckarhausen (DE); Markus Rösch, Dienheim (DE); Andrea Haunert, Mannheim (DE); Markus Schubert, Ludwigshafen (DE)

(73) Assignee: BASF AG, Ludwigshafen (DE)

( * ) Notice: Subject to any disclaimer, the term of this patent is extended or adjusted under 35 U.S.C. 154(b) by 120 days.

(21) Appl. No.: 10/589,049

(22) PCT Filed: Feb. 8, 2005

(86) PCT No.: PCT/EP2005/001235

§ 371 (c)(1),
(2), (4) Date: Aug. 10, 2006

(87) PCT Pub. No.: WO2005/077871

PCT Pub. Date: Aug. 25, 2005

(65) Prior Publication Data

US 2007/0135648 A1 Jun. 14, 2007

(30) Foreign Application Priority Data

Feb. 13, 2004 (DE) .............. 10 2004 007 499

(51) Int. Cl.
*C07C 31/18* (2006.01)
*C07C 53/00* (2006.01)
(52) U.S. Cl. .................. 568/852; 562/852
(58) Field of Classification Search .............. None
See application file for complete search history.

(56) References Cited

U.S. PATENT DOCUMENTS

| 4,659,686 A | 4/1987 | Griffiths et al. |
| 5,187,136 A * | 2/1993 | Klobucar et al. ............ 502/162 |
| 5,536,879 A | 7/1996 | Antons et al. |
| 5,731,479 A | 3/1998 | Antons et al. |
| 6,310,254 B1 | 10/2001 | Antons et al. |
| 6,355,848 B1 * | 3/2002 | Antons et al. ............. 568/881 |
| 6,376,414 B1 | 4/2002 | Antons et al. |
| 7,217,847 B2 * | 5/2007 | Fischer et al. ............ 568/814 |
| 2006/0116521 A1 | 6/2006 | Fischer et al. |

FOREIGN PATENT DOCUMENTS

| EP | 0 147 219 | 7/1985 |
| EP | 0 696 575 | 2/1996 |
| EP | 0 717 023 | 6/1996 |
| EP | 1 051 388 | 11/2000 |
| WO | WO-99/38613 | 8/1999 |
| WO | WO-99/38824 | 8/1999 |
| WO | WO-99/38838 | 8/1999 |
| WO | WO-2004/022522 | 3/2004 |

* cited by examiner

*Primary Examiner*—Karl J Puttlitz
(74) *Attorney, Agent, or Firm*—Connolly Bove Lodge & Hutz LLP

(57) ABSTRACT

The present invention relates to a process for preparing optically active hydroxy-, alkoxy-, amino-, alkyl-, aryl- or chlorine-substituted alcohols or hydroxy carboxylic acids having from 3 to 25 carbon atoms or their acid derivatives or cyclization products by hydrogenating the correspondingly substituted optically active mono- or dicarboxylic acids or their acid derivatives in the presence of a catalyst whose active component consists of rhenium or of rhenium and comprises at least one further element having an atomic number of from 22 to 83, with the provisos that a. the at least one further element having an atomic number of from 22 to 83 is not ruthenium and
b. in the case of the preparation of optically active 2-amino-, 2-chloro-, 2-hydroxy- and 2-alkoxy-1-alkanols by catalytically hydrogenating corresponding optically active 2-aminocarboxylic acids, 2-chlorocarboxylic acids, 2-hydroxycarboxylic acids and 2-alkoxycarboxylic acids or their acid derivatives, the at least one further element having an atomic number of from 22 to 83 is not palladium or platinum.

17 Claims, No Drawings

METHOD FOR PRODUCING OPTICALLY ACTIVE ALCOHOLS OR CARBOXYLIC ACIDS

RELATED APPLICATIONS

This application is a national stage application (under 35 U.S.C. 371) of PCT/EP2005/001235 filed Feb. 8, 2005, which claims benefit to German application 10 2004 007 499.2 filed Feb. 13, 2004.

The present invention relates to a process for preparing optically active hydroxy-, alkoxy-, amino-, alkyl-, aryl- or chlorine-substituted alcohols or hydroxy carboxylic acids having from 3 to 25 carbon atoms or their acid derivatives or cyclization products by hydrogenating the correspondingly substituted optically active mono- or dicarboxylic acids or their acid derivatives.

The target compounds mentioned constitute valuable intermediates for the pharmaceuticals and cosmetics industry for the preparation of medicaments, fragrances and other organic fine chemicals which are difficult to obtain inexpensively.

EP-A 0696575 describes a process for preparing optically active amino alcohols by hydrogenating the corresponding amino acids in the presence of Ru catalysts reduced with hydrogen at temperatures of from 50 to 150° C. and pressures of from 5 to 300 bar.

EP-A 0717023 relates to a process for preparing optically active alcohols by reducing the corresponding optically active carboxylic acids in the presence of Ru catalysts reduced with hydrogen at temperatures of <160° C. and pressures of <250 bar.

WO 99/38838 describes a process for preparing optically active amino alcohols by catalytically hydrogenating the corresponding amino acids with bi- or trimetallic unsupported or supported Ru catalysts with addition of acid.

WO 99/38613 the preparation of unsupported hydrogenation catalysts which comprise ruthenium and at least one further metal having an atomic number of from 22 to 83. Using these catalysts, it is possible to hydrogenate carboxylic acids and their derivatives under mild conditions. In the case of enantiomerically pure substrates, the achievable enantiomeric success is a maximum of 98.8% at yields below 80%.

WO 99/38824 describes a process for preparing optically active alcohols by reducing optically active carboxylic acids in the presence of Ru catalysts which have been reduced with hydrogen and comprise at least one further metal having an atomic number in the range from 22 to 83.

EP-A 1051388 describes unsupported Ru/Re suspension catalysts by which chiral α-amino acids or α-hydroxy acids can be reduced at from 60 to 100° C. and 200 bar of hydrogen pressure to the corresponding chiral alcohols.

U.S. Pat. No. 4,659,686 discloses that, using alkali metal- or alkaline earth metal-doped catalysts which comprise a Pt group metal and Re on carbon in the hydrogenation of malic acid, the reaction products formed are tetrahydrofuran (THF) and/or butanediol (BDO). 1,2,4-Butanetriol is not found using these catalysts.

EP-A 147 219 describes Pd—Re catalysts and their use in a process for preparing THF and BDO. Example 39 shows that the hydrogenation of malic acid at 200° C. and 170 bar leads in yields of 66% to THF and of 21% to BDO. 1,2,4-Butanetriol is not found.

Adv. Synth. Catal. 2001, 343, No. 8 describes the use of the Nishimura catalyst (Rh—Pt oxide) for the racemization-free hydrogenation of α-amino acid esters and α-hydroxy carboxylic esters. However, large amounts (10% by weight) of the expensive catalyst system are required there. Moreover, the free carboxylic acids initially have to be converted to the corresponding esters in a further synthetic step.

A problem in the use of Ru catalysts in the hydrogenation of carboxylic acids is that they have a high tendency to decarbonylate the reactants used or the products obtained to release carbon monoxide. In addition to the associated high pressure rise, the reduction of the carbon monoxide released to methane constitutes a great safety risk.

It is an object of the present invention to provide a process for hydrogenating optically active carboxylic acids or their acid derivatives to the corresponding optically active alcohols, in which the undesired decarbonylation of the reactants used or the products formed is very substantially prevented.

According to the invention, this object is achieved by providing a process for preparing optically active hydroxy-, alkoxy-, amino-, alkyl-, aryl- or chlorine-substituted alcohols or hydroxy carboxylic acids having from 3 to 25 carbon atoms or their acid derivatives or cyclization products by hydrogenating the correspondingly substituted optically active mono- or dicarboxylic acids or their acid derivatives in the presence of a catalyst whose active component consists of rhenium or of rhenium and comprises at least one further element having an atomic number of from 22 to 83, with the provisos that a. the at least one further element having an atomic number of from 22 to 83 is not ruthenium and b. in the case of the preparation of optically active 2-amino-, 2-chloro-, 2-hydroxy- and 2-alkoxy-1-alkanols by catalytically hydrogenating corresponding optically active 2-aminocarboxylic acids, 2-chlorocarboxylic acids, 2-hydroxycarboxylic acids and 2-alkoxycarboxylic acids or their acid derivatives, the at least one further element having an atomic number of from 22 to 83 is not palladium or platinum.

The process according to the invention is suitable for hydrogenating optically active mono- or dicarboxylic acids having from 3 to 25, preferably having from 3 to 12, carbon atoms, which may be straight-chain, branched or cyclic and have at least one, typically from 1 to 4, substituents each bonded to an asymmetrically substituted carbon atom. The process is equally suitable for hydrogenating acid derivatives of the substituted carboxylic acids mentioned. Here, as within the entire context of the present invention, the term acid derivative means that the acid function is present in the form of an ester, a partial ester, an anhydride or an amide, preferably in the form of an ester or partial ester.

In the context of the present invention, optically active compounds refer to those compounds which are capable, as such or in dissolved form, of rotating the plane of polarization of linear-polarized light passing through. Compounds having a stereogenic center are nonracemic mixtures of the two enantiomers, i.e. mixtures in which the two enantiomers are not present in equal parts. In the case of the conversion of compounds having more than one stereocenter, different diastereomers may be obtained which, each viewed alone, are to be regarded as optically active compounds.

Possible substituents bonded to asymmetrically substituted carbon atoms include: hydroxyl, alkoxy, amino, alkyl, aryl or chlorine substituents, and alkoxy substituents refer in particular to those whose organic radical bonded to the oxygen atom has from 1 to 8 carbon atoms, amino substituents may be present in the form of the free amine or preferably in protonated form as the ammonium salt and if appropriate having one or two organic radicals each having from 1 to 5 carbon atoms, the alkyl substituents have from 1 to 10 carbon atoms and the aryl substituents from 3 to 14 carbon atoms and may themselves bear substituents which are stable under the reaction conditions, and the aryl substituents may also have from 1 to 3 heteroatoms, for example N, S and/or O.

The substituents mentioned may in principle be attached at any possible point on the mono- or dicarboxylic acid to be converted. Preferred substrates in the context of the present invention are those which have at least one of the substituents mentioned which have on an asymmetric carbon atom in the α- or β-position, more preferably in the α-position to the acid function to be hydrogenated.

In the case of the conversion of dicarboxylic acids, the inventive hydrogenation reaction may, as desired, be conducted in such a way that either only one or both of the carboxylic acids functions or carboxylic acid derivative functions present in the substrate molecule are hydrogenated to the hydroxyl functions.

For example, the process according to the invention is suitable for converting optically active carboxylic acids or their acids derivatives of the formula I

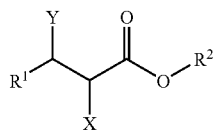

(I)

in which the radicals are each defined as follows:

$R^1$: straight-chain and branched $C_1$-$C_{12}$-alkyl, $C_7$-$C_{12}$-aralkyl or $C_6$-$C_{14}$-aryl, where the radicals mentioned may be substituted by $NR^3R^4$, OH, COOH and/or further groups stable under the reaction conditions, $R^2$: hydrogen, straight-chain or branched $C_1$-$C_{12}$-alkyl or $C_3$-$C_8$-cycloalkyl, X, Y:
  each independently hydrogen, chlorine, $NR^5R^6$ or $OR^7$, straight-chain or branched $C_1$-$C_{10}$-alkyl or $C_6$-$C_{14}$-aryl, with the proviso that at least one of the X or Y radicals is not hydrogen, X and $R^1$ or Y and $R^1$:
  together may also be a 5- to 8-membered cycle, $R^3$, $R^4$, $R^5$ and $R^6$:
  each independently hydrogen, straight-chain and branched $C_1$-$C_{12}$-alkyl, $C_7$-$C_{12}$-aralkyl, $C_6$-$C_{14}$-aryl, $C_3$-$C_8$-cycloalkyl or $C_3$-$C_8$-cycloalkyl in which one $CH_2$ group has been replaced by O or $NR^8$, $R^3$ and $R^4$, and $R^5$ and $R^6$:
  each independently together also $-(CH_2)_m-$, where m is an integer from 4 to 7, $R^1$ and $R^5$:
  together also $-(CH_2)_n-$, where n is an integer from 2 to 6, $R^7$: hydrogen, straight-chain or branched $C_1$-$C_{12}$-alkyl or $C_3$-$C_8$-cycloalkyl, $R^1$ and $R^7$:
  together also $-(CH_2)_n-$, where n is an integer from 2 to 6 and $R^8$: hydrogen, straight-chain or branched $C_1$-$C_{12}$-alkyl, $C_7$-$C_{12}$-aralkyl or $C_6$-$C_{14}$-aryl, or their acid anhydrides to the corresponding optically active alcohols.

The $R^1$ radicals may be varied widely and may also bear, for example, from 1 to 3 substituents stable under the reaction conditions such as $NR^3R^4$, OH and/or COOH.

Examples of $R^1$ Radicals Include the Follow:

$C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, $C_1$-$C_{12}$-alkyl such as $C_1$-$C_6$-alkyl (mentioned above) or unbranched or branched heptyl, octyl, nonyl, decyl, undecyl or dodecadecyl, $C_7$-$C_{12}$-aralkyl such as phenylmethyl, 1-phenylethyl, 2-phenylethyl, 1-phenylpropyl, 2-phenylpropyl or 3-phenylpropyl, $C_6$-$C_{14}$-aryl such as phenyl, naphthyl or anthracenyl, where the aromatic radicals may bear substituents such as $NR^9R^{10}$, OH and/or COOH.

Examples of definitions for $R^2$ are as Follows:

hydrogen, straight-chain or branched $C_1$-$C_{12}$-alkyl (as mentioned above) or $C_3$-$C_8$-cycloalkyl, for example cyclopropyl, cyclobutyl, cyclopentyl, cyclohexyl, cycloheptyl and cyclooctyl.

Instead of the carboxylic esters, the carboxylic acid derivatives used may also be the acid anhydrides.

The X and Y radicals are each independently chlorine, $NR^5R^6$ or $OR^7$, where $R^5$ and $R^6$, just like $R^3$ and $R^4$, or $R^9$ and $R^{10}$, are each independently hydrogen, straight-chain and branched $C_1$-$C_{12}$-alkyl, in particular $C_1$-$C_6$-alkyl, $C_7C_{12}$-aralkyl or $C_6$-$C_{14}$-aryl, in particular phenyl, or $C_3$-$C_8$-cycloalkyl (in each case as mentioned above for the $R^1$ and $R^2$ radicals), and where at least one of the X and Y radicals is not hydrogen.

The X and $R^1$ or Y and $R^1$ radicals may also together be a 5- to 8-membered, saturated or unsaturated and optionally substituted ring, for example a cyclopentyl, a cyclohexyl or a cyclooctyl radical.

The $R^3$ and $R^4$, $R^5$ and $R^6$, and $R^9$ and $R^{10}$ radicals may together each independently also be $-(CH_2)_m-$ where m is an integer from 4 to 7, in particular 4 or 5. One $CH_2$ group may be replaced by O or $NR^8$.

The $R^1$ and $R^5$ radicals together may also be $-(CH_2)_n-$ where n is an integer from 2 to 6.

The $R^7$ radical is preferably hydrogen or straight-chain or branched $C_1$-$C_{12}$-alkyl or $C_3$-$C_8$-cycloalkyl, more preferably methyl, ethyl, 1-methylethyl, 1,1-dimethylethyl, hexyl, cyclohexyl or dodecyl. Together with $R^1$, it may also be $-(CH_2)_n-$, where n is an integer from 2 to 6.

In the case of the preparation of optically active 2-amino-, 2-chloro-, 2-hydroxy- and 2-alkoxy-1-alkanols in the presence of catalysts comprising palladium and rhenium or platinum and rhenium, 2-amino-, 2-chloro-, 2-hydroxy- and 2-alkoxycarboxylic acids and their acid derivatives are excluded from the group of the compounds to be converted in accordance with the invention.

The process according to the invention is also suitable for converting optically active dicarboxylic acids or their acid derivatives, in particular those of the formula (II)

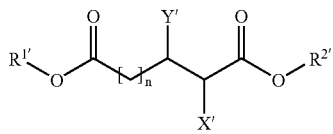

(II)

where
X', Y': each independently hydrogen, chlorine, $NR^{5'}R^{6'}$ or $OR^{7'}$, straight-chain or branched $C_1$-$C_{10}$-alkyl or $C_6$-$C_{10}$-aryl, with the proviso that at least one of the X' or Y' radicals is not hydrogen,
$R^{1'}$, $R^{2'}$: each independently hydrogen, straight-chain or branched $C_1$-$C_2$-alkyl or $C_3$-$C_8$-cycloalkyl and
n is an integer from 0 to 8
$R^{5'}$, $R^{6'}$: each independently hydrogen, straight-chain and branched $C_1$-$C_{12}$-alkyl, $C_7$-$C_{12}$-aralkyl, $C_6$-$C_{14}$-aryl, $C_3$-$C_8$-cycloalkyl or $C_3$-$C_8$-cycloalkyl, in which one $CH_2$ group is replaced by O or $NR^8$, and, together, is also —$(CH_2)_m$—, where m is an integer from 4 to 7,
$R^{7'}$: hydrogen, straight-chain or branched $C_1$-$C_{12}$-alkyl or $C_3$-$C_8$-cycloalkyl and
$R^{8'}$: hydrogen, straight-chain or branched $C_1$-$C_{12}$-alkyl, $C_7$-$C_{12}$-aralkyl or $C_6$-$C_{14}$-aryl to the corresponding optically active hydroxy carboxylic acids or their acid derivatives or, in the case of the hydrogenation of both carboxylic acid functions, to the corresponding optically active substituted diols. For example, it is also possible to hydrogenate optically active hydroxy dicarboxylic acids to the corresponding optically active triols.

$R^{1'}$ and $R^{2'}$ may, by way of example and each independently, assume the following definitions: hydrogen, straight-chain or branched $C_1$-$C_2$-alkyl (as specified above for radical $R^1$ in formula I) or $C_3$-$C_8$-cycloalkyl, for example, cyclopropyl, cyclobutyl, cyclopentyl, cyclohexyl, cycloheptyl and cyclooctyl.

Instead of the carboxylic esters, the carboxylic acid derivatives used may also be the acid anhydrides.

The X' and Y' radicals are each independently hydrogen, chlorine, $NR^{5'}R^{6'}$ or $OR^{7'}$, where $R^{5'}$ and $R^{6'}$ are each independently hydrogen, straight-chain and branched $C_1$-$C_{12}$-alkyl, in particular $C_1$-$C_6$-alkyl, $C_7$-$C_{12}$-aralkyl or $C_6$-$C_{14}$-aryl, in particular phenyl, or $C_3$-$C_8$-cycloalkyl (in each case as specified above for the $R^1$ and $R^2$ radicals in formula I).

The $R^{5'}$ and $R^{6'}$ radicals may each independently together also be —$(CH_2)_m$— where m is an integer from 4 to 7, in particular 4 or 5. One $CH_2$ group may be replaced by O or $NR^{8'}$.

The $R^{7'}$ radical is preferably hydrogen or straight-chain or branched $C_1$-$C_{12}$-alkyl or $C_3$-$C_8$-cycloalkyl, more preferably methyl, ethyl, 1-methylethyl, 1,1-dimethylethyl, hexyl, cyclohexyl or dodecyl.

The optically active hydroxy carboxylic acids or diols obtainable by the process according to the invention by hydrogenating optically active dicarboxylic acids, for example those of the formula II, may, under suitable conditions, also form optically active cyclization products by intramolecular cyclization, for example lactones, lactams or cyclic ethers. Preferred cyclization products are the lactones and cyclic ethers, whose preparation in optically active form by hydrogenation of optically active dicarboxylic acids and subsequent cyclization also forms part of the subject matter of this invention. Preferred optically active lactones obtainable in the inventive manner starting from optically active dicarboxylic acids of the formula II are, for example, those of the formula III or IV

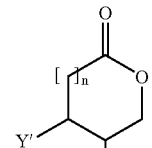

(III)

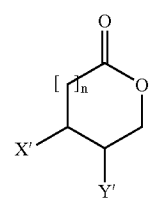

(IV)

where the X', Y' radicals and n are each as defined for formula II.

Preferred cyclic ethers obtainable in optically active form in the inventive manner starting from optically dicarboxylic acids of the formula II are, for example, those of the formula V or VI

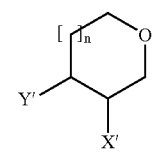

(V)

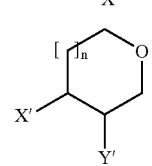

(VI)

where the X', Y' radicals and n are each as defined for formula II.

In this way, the process according to the invention makes available, for example, the following lactones in optically active form: 2-hydroxy-γ-butyrolactone, 3-hydroxy-γ-butyrolactone, 2-chloro-γ-butyrolactone, 3-chloro-γ-butyrolactone, 2-amino-γ-butyrolactone, 3-amino-γ-butyrolactone, 2-methyl-γ-butyrolactone, 3-methyl-γ-butyrolactone, 3-hydroxy-δ-valerolactone, 4-hydroxy-δ-valerolactone.

Among these, particular preference in the context of the inventive preparative process is given to 3-hydroxy-γ-butyrolactone in optically active form.

Examples of cyclic ethers made available in optically active form by the process according to the invention include: 2-hydroxytetrahydrofuran, 2-methyltetrahydrofuran and 2-aminotetrahydrofuran.

A preferred embodiment of the process according to the invention relates to the preparation of optically active 3-hydroxy-, 3-alkoxy-, 3-amino-, 3-alkyl-, 3-aryl- or 3-chloro-1-alkanols starting from the correspondingly substituted optically active 3-hydroxy-, 3-alkoxy-, 3-amino-, 3-alkyl-, 3-aryl- or 3-chloromonocarboxylic acids or their acid derivatives using catalysts comprising palladium and rhenium or platinum and rhenium.

It is thus possible in the inventive manner, using catalysts comprising palladium and rhersium or platinum and rhenium, to obtain 3-hydroxy-, 3-alkoxy-, 3-amino-, 3-alkyl-, 3-aryl- or 3-chloroalcohols or diols, for example, by converting optically active carboxylic acids or their acid derivatives of the formula VII

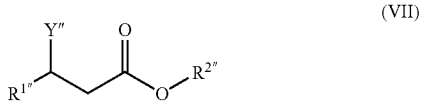

in which the radicals are each defined as follows:
$R^{1''}$: straight-chain and branched $C_1$-$C_{12}$-alkyl, $C_7$-$C_{12}$-aralkyl or $C_6$-$C_{14}$-aryl, where the radicals mentioned may each be substituted by $NR^{3''}R^{4''}$, OH, $COOR^{2'''}$ and/or further groups stable under the reaction conditions,
$R^{2''}$, $R^{2'''}$: each independently hydrogen, straight-chain or branched $C_1$-$C_{12}$-alkyl or $C_3$-$C_8$-cycloalkyl,
Y'': chlorine, $NR^{5''}R^{6''}$ or $OR^{7''}$, straight-chain or branched $C_1$-$C_{10}$-alkyl or $C_6$-$C_{14}$-aryl,
$R^{3''}$, $R^{4''}$, $R^{5''}$ and $R^{6''}$:
each independently hydrogen, straight-chain and branched $C_1$-$C_{12}$-alkyl, $C_7$-$C_{12}$-aralkyl, $C_6$-$C_{14}$-aryl, $C_3$-$C_8$-cycloalkyl or $C_3$-$C_8$-cycloalkyl in which one $CH_2$ group has been replaced by O or $NR^{8''}$.
$R^{3''}$ and $R^{4''}$, and $R^{5''}$ and $R^{6''}$:
each independently together also —$(CH_2)_m$— where m is an integer from 4 to 7,
$R^{1''}$ and $R^{5''}$:
together also —$(CH_2)_n$— where n is an integer from 2 to 6,
$R^{7''}$: hydrogen, straight-chain or branched $C_1$-$C_{12}$-alkyl or $C_3$-$C_8$-cycloalkyl,
$R^{1''}$ and $R^{7''}$:
together also —$(CH_2)_n$— where n is an integer from 2 to 6 and
$R^{8''}$: hydrogen, straight-chain or branched $C_1$-$C_{12}$-alkyl, $C_7$$C_{12}$-aralkyl or $C_6$-$C_{10}$-aryl.

Examples of radicals specified correspond to those mentioned for the radicals in formula I.

A further preferred embodiment of the process according to the invention relates to the preparation of optically active 2-alkyl- and 2-aryl-1-alkanols starting from the correspondingly substituted optically active 2-alkyl- and 2-arylcarboxylic acids respectively or their acid derivatives using catalysts comprising palladium and rhenium or platinum and rhenium. The alkyl and aryl substituents are each as defined for the X and Y radicals in formula I.

Examples of preferred compounds obtainable in optically active form by the process according to the invention include:
1,2- and 1,3-amino alcohols, for example: α-alaninol, and also, in each case in the α- or β-form: leucinol, isoserinol, valinol, isoleucinol, serinol, threoninol, lysinol, phenylalaninol, tyrosinol, prolinol, and also the alcohols obtainable from the amino acids ornithine, citrulleine, aspartine, aspartic acid, glutamine and glutamic acid, by converting the corresponding optically active α- or β-amino acids or their acid derivatives,
1,2- and 1,3-alkanediols, for example: 1,2-propanediol, 1,2-butanediol, 1,2-pentanediol, 1,3-pentanediol by converting the corresponding optically active α- or β-hydroxy-carboxylic acids or their acid derivatives,
1,2- and 1,3-chloroalcohols, for example 2-chloropropanol, by converting the corresponding optically active α- or β-chlorocarboxylic acids, α- or β-chloro-dicarboxylic acids or their acid derivatives,
1,2- and 1,3-alkylalcohols, for example 2-methyl-1-butanol, 2,3-dimethyl-butane-1,4-diol, 2-methylbutane-1,4-diol, by converting the corresponding optically active α- or β-alkylcarboxylic acids or their acid derivatives,
triols, for example 1,2,4-butanetriol, 1,2,5-pentanetriol, 1,2,6-hexanetriol, by converting the corresponding optically active α- or β-hydroxyhydroxydicarboxylic acids and dihydroxycarboxylic acids or their acid derivatives, for example 3,4-dihydroxybutyric acid, by converting the corresponding optically active dicarboxylic acids.

Suitable for carrying out the hydrogenation process according to the invention are those catalysts whose active component consists of Re, for example of Re sponges or rhenium on a suitable support, for example Re on activated carbon, $TiO_2$, $ZrO_2$ or high-surface activated graphite, or those catalysts whose active component comprises rhenium and at least one further element having an atomic number of from 22 to 83, the at least one further element having an atomic number of from 22 to 83 not being ruthenium.

Preferred catalysts in the context of the process according to the invention are those whose active component comprises rhenium and at least one further element selected from the group of the elements: Rh, Ir, Cu, Ag, Au, Cr, Mo, W, Co and Ni.

Particular preference is given to those catalysts whose active component comprises rhenium and at least one further element selected from the group of the elements: Pd, Pt, Rh, Ir. Special preference is given to those catalysts whose active component consists of Re and a further element selected from the group of the elements: Pd, Pt, Rh, Ir. Among these, preference is in turn given to those catalysts whose active component consists of Re and a further element selected from the group of the elements: Rh, Ir.

The inventive catalysts may be used with good success as unsupported or as supported catalysts. Supported catalysts have the feature that the selected active component has been applied to the surface of a suitable support. To carry out the inventive hydrogenation process, particular preference is given to supported catalysts which have a high surface area and therefore require smaller amounts of the active metals.

The unsupported catalysts can be prepared, for example, by reducing a slurry and/or solution in aqueous or organic medium of rhenium and a further inventive active component in metallic form or in the form of compounds, for example oxides, oxide hydrates, carbonates, nitrates, carboxylates, sulfates, phosphates, halides, Werner complexes, organometallic complexes or chelate complexes or mixtures thereof.

When the catalysts are used in the form of supported catalysts, preference is given to supports such as charcoals, carbon blacks, graphites, high-surface activated graphite (HSAG), $SiO_2$, $Al_2O_3$, $TiO_2$, $ZrO_2$, SiC, clay earths, silicates, montmorillonites, zeolites or mixtures thereof. For use as support materials, particular preference is given to charcoals, graphites, HSAG, $TiO_2$ and $ZrO_2$.

In the case of the carbon-based supports (activated carbons, graphites, carbon blacks, HSAG), it is advantageous in accordance with the invention to treat the support material oxidatively with customary antioxidants, for example $HNO_3$, $H_2O_2$, $O_2$, air, $O_3$, ammonium persulfate, sodium hypochlorite, hypochlorous acid, perchloric acid, nitrate salts, and/or with acids such as $HNO_3$, $H_3PO_4$, HCl or HCOOH. Particular preference is given to pretreating with $HNO_3$, $H_3PO_4$ or HCOOH. The support may be treated before or during the application of the metals. The pretreatment allows activity and selectivity of the supported catalysts in the inventive hydrogenation to be improved.

The inventive supported catalysts typically comprise from about 0.01 to 50% by weight of rhenium in metallic form or in the form of compounds and from 0.01 to 30% by weight of at least one further element having an atomic number of from 22 to 83, excluding ruthenium, in metallic form or in the form of a compound or mixtures thereof. The % by weight data are in each case based on the total weight of the catalysts and calculated in metallic form.

The proportion of rhenium, calculated as a metal, is preferably from about 0.1 to 30% by weight, more preferably from about 1 to 20% by weight, based on the total weight of the supported catalyst.

The proportion of the at least one further element having an atomic number of from 22 to 83, excluding ruthenium, is preferably from about 0.1 to 20% by weight and more preferably from about 1 to 10% by weight, based on the total weight of the finished supported catalyst.

The rhenium component used is typically $Re_2O_7$, $ReO_2$, $ReCl_3$, $ReCl_5$, $HReO_4$, $Re(CO)_5Cl$, $Re(CO)_5Br$, or $Re_2(CO)_{10}$ or rhenium complexes. Particular preference is given to $Re_2O_7$ and $HReO_4$.

The further elements, in addition to rhenium, having an atomic number of from 22 to 83, excluding ruthenium, are typically applied to the support material in the form of metal, oxides, oxide hydrates, carbonates, nitrates, carboxylates, sulfates, phosphates, Werner complexes, chelate complexes or halides. Preference is given to compounds of Pt, Pd, Rh or Ir. Special preference is given to Ir and Rh in the form of the nitrates.

The application of the active components may be prepared in one or more steps by impregnation with an aqueous or alcoholic solution of the particular dissolved salts or oxides or of dissolved oxidic or metallic colloids, or by equilibrium adsorption in one or more steps of the salts or oxides dissolved in aqueous or alcoholic solution, or of dissolved oxidic or metallic colloids. Between individual equilibrium adsorption or impregnation steps, a drying step may in each case be carried out to remove the solvent and, if desired, a calcination step or reduction step.

The drying is advantageously carried out in each case at temperatures of from about 25 to about 350° C., preferably from about 40 to about 280° C., and more preferably from about 50 to about 150° C.

If desired, a calcination after each application or drying step at temperatures in the range from about 100 to 800° C., preferably from about 200 to about 600° C. and more preferably from about 300 to about 500° C.

If desired, a reduction may be carried out after each application step.

In a particular embodiment of the preparation of the supported catalysts usable in accordance with the invention, a metal having an atomic number of from about 22 to 83, excluding ruthenium, is applied to the support in a first impregnation step from the particular oxides, oxide hydrates, carbonates, nitrates, carboxylates, sulfates, phosphates, Werner complexes, chelate complexes or halides, then there is a drying step and, if desired, a calcination step and, if desired, a reduction step. Afterward, there is, if desired, a further impregnation with one or more metals having an atomic number of from 22 to 83, excluding ruthenium, from the particular oxides, oxide hydrates, carbonates, nitrates, carboxylates, sulfates, phosphates, Werner complexes, chelate complexes or halides with subsequent drying and, if desired, calcination. In the last preparation step, rhenium is then applied to the support in the form of $Re_2O_7$, $ReO_2$, $ReCl_3$, $ReCl_5$, $HReO_4$, $Re(CO)_5Cl$, $Re(CO)_5Br$, or $Re_2(CO)_{10}$. Finally, there is a further drying step, and, if desired, a calcination step.

A further means of preparing the inventive supported catalysts consists in the electroless deposition on the support material of rhenium and at least one further metallic component having an atomic number of from 22 to 83, excluding ruthenium, from the particular oxides, oxide hydrates, carbonates, nitrates, carboxylates, sulfates, phosphates, Werner complexes, chelate complexes or halides. The electroless deposition is advantageously effected in aqueous or alcoholic slurry of the support material and the particular metal compounds by adding reducing agents, for example alcohols or sodium hypophosphite, formic acid, alkali metal formates, in particular sodium formates. Particular preference is given to ethanol and $NaH_2PO_2$.

After the deposition, a drying step is advantageously carried out at temperatures in the range from about 25 to about 350° C., preferably from about 40 to about 280° C. and more preferably from about 50 to about 150° C.

If desired, a calcination may be effected after the deposition at temperatures in the range from about 100 to about 800° C., preferably from about 200 to about 600° C. and more preferably from about 300 to about 500° C.

The catalysts used in accordance with the invention are typically activated before used. In the case of the catalysts prepared by electroless deposition, this activation step may, if desired, be dispensed with. Preference is given to activating using hydrogen or a mixture of hydrogen and an inert gas, typically a mixture of $H_2$ and $N_2$. The activation is carried out at temperatures of from 100 to about 500° C., preferably from about 140 to about 400° C. and more preferably from about 180 to about 330° C. Activation is effected at pressures of from about 1 bar to about 300 bar, preferably from about 5 to about 200 bar and more preferably from about 10 to about 100 bar.

The catalysts usable in accordance with the invention typically have a specific surface area of from about 5 to 3000 $m^2/g$, preferably from about 10 to about 1500 $m^2/g$.

The inventive hydrogenation reaction typically proceeds in the presence of hydrogen at temperatures in the range from about 10 to about 300° C., preferably from about 30 to about 180° C. and more preferably from about 50 to 130° C. In general, a pressure of from about 1 to about 350 bar, preferably from about 10 to about 300 bar and more preferably from about 100 to about 300 bar is employed.

In the case of the inventive hydrogenation of optically active dicarboxylic acids to the corresponding optically active diols, preference is given to selecting a pressure of from about 150 to about 250° C., more preferably from about 180 to about 250° C. and most preferably from about 200 to about 250° C.

In a preferred embodiment of the process according to the invention, especially for hydrogenating amino-substituted substrates, the above-described optically active starting materials are hydrogenated in the presence of an organic or inorganic acid. In general, the addition of acid is from 0.5 to 1.5 equivalents, more preferably from 1 to 1.3 equivalents, based on 1 equivalent of any basic groups present in the starting materials. Useful organic acids include, for example, acetic acid, propionic acid and adipic acid. Preference is given to adding inorganic acids, especially sulfuric acid, hydrochloric acid and phosphoric acid. The acids may be used, for example, as such, in the form of aqueous solutions or in the form of their separately prepared salts with the starting materials to be hydrogenated, for example as sulfates, hydrogensulfates, hydrochlorides, phosphates, mono- or dihydrogenphosphates.

The optically active carboxylic acid or dicarboxylic acid to be converted may be used with good success in substance or in the form of an aqueous or organic solution. The hydrogenation may be carried out in suspension or in the liquid or gas phase in the fixed bed reactor in continuous mode.

In the case of a batchwise reaction, for example, from 0.1 to 50 g of the unsupported catalysts to be used in accordance with the invention or else from 0.1 to 50 g of supported catalysts to be used in accordance with the invention may be used based on 1 mole of optically active starting compound used.

In a continuous process, the ratio of catalyst to starting compound to be converted is advantageously converted in such a way that a catalyst hourly space velocity in the range from about 0.005 to about 2 kg/$l_{cat}$h, preferably from about 0.02 to about 0.5 kg/$l_{cat}$h.

Suitable solvents for the reaction are, for example, the hydrogenation products themselves, water, alcohols, e.g. methanol, ethanol, propanol, butanol, ethers, e.g. THF or ethylene glycol ether. Preference is given to water or methanol or mixtures thereof as solvents.

The hydrogenation may be carried out in one or more stages in the gas or liquid phase. In the liquid phase, the suspension or fixed bed mode is possible. To carry out the process according to the invention, suitable reactors are all of those known by those skilled in the art to be suitable for carrying out hydrogenations, for example stirred tanks, fixed bed reactors, shaft reactors, tube bundle reactors, bubble columns or fluidized bed reactors.

The reaction is typically complete when no more hydrogen is taken up. Typically the reaction time is from about 1 to about 72 h.

The isolation and, if necessary, separation of the reaction products obtained may in principle be carried out by all customary processes known per se to those skilled in the art. Especially suitable for this purpose are extractive and distillative processes, and also the purification or isolation by crystallization.

The optically active reactants used or products obtained may be investigated for their enantiomeric purity by means of all methods known to those skilled in the art. Particularly suitable for this purpose are in particular chromatographic processes, especially gas chromatography processes or high-performance liquid chromatography (HPLC) processes. A suitable measure for determining the enantiomeric purity of the reactants or products is the enantiomeric excess (ee).

The process according to the invention features substantial suppression in the hydrogenation of the racemization of stereogenic centers of the substituted mono- or dicarboxylic acids used in optically active form as starting compounds. Accordingly, the enantiomeric excess of the products obtained in the process according to the invention typically corresponds substantially to the reactants used. Preference is given to selecting the reaction conditions in such a way that the enantiomeric excess of the desired product corresponds to at least 90%, more preferably to at least 95%, most preferably to at least 98%, of that of the starting compound used.

One advantage of the process according to the invention is that the known troublesome side reaction in those reactions, that of decarbonylation with release of carbon monoxide and its subsequent reduction to methane or other lower alkanes, is substantially suppressed. This leads to considerable safety advantages.

The Following Examples Serve to Illustrate the Process According to the Invention, but without Restricting it in Any Way:

General Procedure for the Activation of the Support Materials by Treating with an Acid:

100 g of the selected support material were heated with 200 ml of the selected acid and 400 ml of water to 100° C. with stirring for 45 min. After filtering off and washing with water, the activated support material was dried at 80° C. in a forced-air oven. When shaped bodies are used, the activation may also be carried out in a rotary evaporator or in a fixed bed reactor flowed through by the activation solution, in order to minimize the mechanical destruction of the support.

Catalyst 1 Preparation Method:

A 2 l stirred apparatus was initially charged with 25 g of Timrex® HSAG 100 (Timcal) pretreated with HCOOH, sodium hypophosphite, 4.9 g of $Re_2O_7$ and 5.4 g of $Pd(NO_3)_2$ in 1400 ml of water, which were stirred at room temperature for 30 min and then at 80° C. Subsequently, the mixture was filtered off through a suction filter, washed and dried.

Catalyst 2 Preparation Method:

A solution of 14 g of $Rh(NO_3)_3$ and 9.8 g of $Re_2O_7$ in 72 ml of water was used to impregnate 100 g of HCOOH-activated Timrex® HSAG 100 (Timcal). Drying for 16 hours was followed by impregnation once again with a solution of 14 g of $Rh(NO_3)_3$ and 9.8 g of $Re_2O_7$ in 72 ml of water and drying once again. Finally, calcination was effected in a rotary tube at 400° C.

Catalyst 3 Preparation Method:

2 g of $Pt(NO_3)_2$ and 3 g of $Re_2O_7$ were dissolved in water and made up to 18 ml with water. This was used to impregnate 25 g of HCOOH-activated Timrex® HSAG 100 which were dried and calcined.

Catalyst 4 Preparation Method:

A solution of 14 g of $Rh(NO_3)_3$ and 9.8 g of $Re_2O_7$ in 72 ml of water was used to impregnate 100 g of $HNO_3$-activated Timrex® HSAG 100 (Timcal). Drying for 16 hours was followed by impregnation once again with a solution of 14 g of $Rh(NO_3)_3$ and 9.8 g of $Re_2O_7$ in 72 ml of water and drying once again. Finally, calcination was effected in a rotary tube at 400° C.

Catalyst 5 Preparation Method:

A solution of 14 g of $Rh(NO_3)_3$ and 9.8 g of $Re_2O_7$ in 72 ml of water was used to impregnate 100 g of $HNO_3$-activated carbon extrudates (3 mm). Drying for 16 hours was followed by impregnation once again with a solution of 14 g of $Rh(NO_3)_3$ and 9.8 g of $Re_2O_7$ in 72 ml of water and drying once again. Finally, calcination was effected in a rotary tube at 400° C.

Catalyst 6 Preparation Method:

4.8 g of $IrCl4.H_2O$ and 4.9 g of $Re_2O_7$ were dissolved in water and made up to 18 ml of water. This was used to impregnate 25 g of HCOOH-activated Timrex® HSAG 100 which were dried and calcined.

Catalyst 7 Preparation Method:

2.7 g of $Pd(NO_3)_2$ and 2.4 g of $Re_2O_7$ were dissolved in water and made up to 18 ml with water. This was used to impregnate 25 g of HCOOH-activated Timrex® HSAG 100. Drying for 16 hours was followed by impregnation once again with a solution of 2.7 g of $Pd(NO_3)_2$ and 2.4 g of $Re_2O_7$ in 18 ml of water and drying once again. Finally, calcination was effected in a rotary tube at 400° C.

Catalyst 8 Preparation Method:

0.6 g of $Pd(NO_3)_2$ was dissolved in water and made up to 18 ml of overall solution. This was used to impregnate 25 g of HCOOH-activated Timrex® HSAG 100 in accordance with its water absorption. After drying for 16 hours and calcining at 400° C. in a rotary tube, a second impregnation was effected, for which 2.9 g of $Re_2O_7$ were dissolved in water and made up to 18 ml of overall solution. This was used to impregnate the material for a second time in accordance with its water absorption and it was dried again for 16 hours.

Catalyst 9 Preparation Method:

0.5 g of $Pt(NO_3)_2$ was dissolved in water and made up to 18 ml of overall solution. This was used to impregnate 25 g of HCOOH-activated Timrex® HSAG 100 in accordance with its water absorption. After drying for 16 hours and calcining at 400° C. in a rotary tube, a second impregnation was effected, for which 3.7 g of $Re_2O_7$ were dissolved in water and made up to 18 ml of overall solution. This was used to impregnate the material for a second time in accordance with its water absorption and it was dried again for 16 hours.

Catalyst 10 Preparation Method:

1.5 g of $Rh(NO_3)_3$ was dissolved in water and made up to 18 ml of overall solution. This was used to impregnate 25 g of HCOOH-activated Timrex® HSAG 100 in accordance with its water absorption. After drying for 16 hours and calcining at 400° C. in a rotary tube, a second impregnation was effected, for which 2 g of $Re_2O_7$ were dissolved in water and made up to 18 ml of overall solution. This was used to impregnate the material for a second time in accordance with its water absorption and it was dried again for 16 hours.

Catalyst 11 Preparation Method:

0.7 g of $Pd(NO_3)_2$ was dissolved in water and made up to 18 ml of overall solution. This was used to impregnate 25 g of HCOOH-activated Timrex® HSAG 100 in accordance with its water absorption. After drying for 16 hours, a second impregnation was effected, for which 5 g of $Ir(CH_3COO)_3$ were dissolved in water and made up to 21.5 ml of overall solution. This was used to impregnate the material for a second time in accordance with its water absorption and it was dried again for 16 hours and finally calcined at 250° C. in a rotary tube.

EXAMPLE 1

Preparation of Optically Active 1,2,4-Butanetriol (BTO)

A batchwise autoclave (capacity 300 ml) was initially charged with 5 g of catalyst 1 with 50 ml of water and stirred at 60 bar of hydrogen pressure and 270° C. for 2 hours. Subsequently, 24 g of malic acid (MA) and 120 g of water were introduced and hydrogenated at a pressure of from 230 to 250 bar and a temperature of 100° C. over a period of 36 h. The reaction effluent comprised 67 mol % of 1,2,4-butanetriol (ee>98.2), 22 mol% of hydroxybutyrolactone (ee>98.2), 5 mol% of butanediol (BDO) and 5 mol% of unconverted malic acid.

EXAMPLES 2-8

Preparation of Optically Active 1,2,4-butanetriol (BTO) with Variation of the Catalyst Example 1 was repeated using the catalysts specified in Table 1 and afforded the results likewise listed in Table 1:

TABLE 1

| Example | Catalyst | 1,2,4-BTO [mol %] | β-HGBL [mol %] | BDO [mol %] | MA [mol %] |
|---|---|---|---|---|---|
| 2 | 3 | 51 ee > 99.2% | 0.3 | 35 | 1 |
| 3 | 2 | 56 ee > 98.6% | — | 14.6 | 2.6 |

TABLE 1-continued

| Example | Catalyst | 1,2,4-BTO [mol %] | β-HGBL [mol %] | BDO [mol %] | MA [mol %] |
|---|---|---|---|---|---|
| 4 | 4 | 70 ee = 97.8% | 0.5 | 1.46 | 0.5 |
| 5*) | 8 | 72 ee = 98.5% | 7 | 6 | 1 |
| 6 | 9 | 48 ee = 99.6% | 5 | 32 | 2 |
| 7 | 10 | 60 ee = 98.2% | 16 | 11 | 2 |
| 8 | 11 | 39 ee = 99.4% | 21 | 9 | 7 |

β-HGBL: β-Hydroxy-γ-butyrolactone,
MA: malic acid,
BDO: 1,4-butanediol
*)The hydrogenation was carried out at a pressure of from 190 to 200 bar over a period of 70 h.

EXAMPLE 9

Preparation of β-Hydroxy-γ-butyrolactone

A batchwise autoclave (capacity 300 ml) was initially charged with 2 g of $Re_2O_7$ and 0.8 g of $PtO_2$ with 50 ml of water and stirred at 60 bar of hydrogen pressure and 270° C. for 2 hours. Subsequently, 24 g of malic acid and 120 g of water were introduced and hydrogenated at a pressure of from 230 to 250 bar and a temperature of 100° C. over a period of 36 h. The reaction effluent comprised 5.9 mol % of 1,2,4-butanetriol, 69 mol % of hydroxybutyrolactone (ee>99.0), 7.7 mol % of butanediol and 27 mol % of unconverted malic acid.

EXAMPLE 10

A batchwise autoclave (capacity 300 ml) was initially charged with 4 g of $Re_2O_7$ with 50 ml of water and stirred at 60 bar of hydrogen pressure and 270° C. for 2 hours. Subsequently, 24 g of malic acid and 120 g of water were introduced and hydrogenated at a pressure of from 230 to 250 bar and a temperature of 100° C. over a period of 36 h. The reaction effluent comprised 6.4 mol % of 1,2,4-butanetriol, 33 mol % of hydroxy-γ-butyrolactone (ee >99.0), 1 mol % of butanediol and 43 mol % of unconverted malic acid.

EXAMPLES 11 and 12

Continuous Hydrogenation of Malic Acid

In a continuous fixed bed hydrogenation, 190 ml of catalyst 5 were initially charged in a fixed bed reactor. At a pressure of 200 bar and a temperature of 100° C., a 6% by weight aqueous solution of malic acid (MA) was passed over the catalyst in trickle mode and in straight pass. With variation of the catalyst hourly space velocity, the results compiled in Table 2 were obtained:

TABLE 2

| Example | Catalyst hourly space velocity [kg MA/I cat *h] | 1,2,4-BTO [mol %] | β-HGBL [mol %] | 1,4-Butanediol [mol %] | MA [mol %] |
|---|---|---|---|---|---|
| 11 | 0.05 | 53 | 12 | 12 | 7 |
| 12 | 0.025 | 58 | 1 | 12 | 2 |

EXAMPLES 13 AND 14 AND COMPARATIVE EXAMPLES 1 AND 2

In a batchwise autoclave (capacity 300 ml), 5 g of the catalyst specified in Table 3 were initially charged with 50 ml of water and stirred with 60 bar of hydrogen pressure and 270° C. for 2 hours. Subsequently, 24 g of malic acid and 120 g of water were introduced and hydrogenated at a pressure of from 230 to 250 bar and a temperature of 160° C. over a period of 36 h. After 36 h, the gases in the autoclave are analyzed. The components listed in Table 3 are detected in the headspace.

TABLE 3

| | | Components in the head space [%]** | | | | |
|---|---|---|---|---|---|---|
| Example | Catalyst | $H_2$ | Methane | Ethane | Propane | Butane |
| 9 | 2 | 95.8 | 2.7 | 0.8 | 0.5 | 0.6 |
| 10 | 7 | 97.7 | 0.3 | — | 0.04 | 0.05 |
| Comparative Example 1 | 8% Ru, 11% Re on HSAG* | 85 | 9.5 | 1.2 | 3.4 | 2.5 |
| Comparative Example 2*** | Ru/Re black | 94.1 | 2.5 | 0.8 | 1.1 | 1.7 |

*HSAG = High surface activated graphite;
**% data in % by vol. (deviation of the sum from 100% resulting from analytical process;
***hydrogenation temperature 100° C.

EXAMPLES 15 AND 16 AND COMPARATIVE EXAMPLE 3

A batchwise autoclave (capacity 300 ml) was initially charged with 5 g of the catalyst specified in Table 3 with 50 ml of water and stirred at 60 bar of hydrogen and 270° C. for 2 hours. Subsequently, 24 g of maleic acid and 120 g of water were introduced and hydrogenation was effected at a pressure of from 230 to 250 bar and a temperature of 100° C. over a period of 36 h. After 36 h, the gases present in the autoclave were analyzed. The components complied in Table 4 are detected in the headspace.

TABLE 4

| Example | Catalyst | $H_2$ | Methane | Ethane | Propane | Butane |
|---|---|---|---|---|---|---|
| 15 | 8 | 99.6 | 0.1 | 7 ppm | 20 ppm | 107 ppm |
| 16 | 9 | 98.8 | 0.1 | 17 ppm | 58 ppm | 554 ppm |
| Comparative Example 3 | Ru/Re black | 98 | 304 ppm | 7 ppm | 8 ppm | 23 ppm |

EXAMPLE 17

Preparation of Alaninol

A batchwise autoclave (capacity 300 ml) was initially charged with 5 g of catalyst 6 with 50 ml of water and stirred at 60 bar of hydrogen pressure and 270° C. for 2 hours. Subsequently, 24 g of L-alanine, 100 g of water and 13.2 g of $H_2SO_4$ are introduced and hydrogenated at a pressure of 180 to 200 bar and a temperature of 100° C. over a period of 12 h. The reaction effluent contained 57 mol % of L-alaninol (ee>99.4) and 12 mol % of unconverted L-alanine.

EXAMPLE 18

Preparation of Alaninol

A batchwise autoclave (capacity 300 ml) was initially charged with 5 g of catalyst 4 with 50 ml of water and stirred at 60 bar of hydrogen pressure and 270° C. for 2 hours. Subsequently, 24 g of L-alanine, 100 g of water and 13.2 g of $H_2SO_4$ are introduced and hydrogenated at a pressure of 180 to 200 bar and a temperature of 100° C. over a period of 12 h. The reaction effluent contained 43 mol % of L-alaninol (ee>99.4) and 40 mol % of unconverted L-alanine.

We claim:

1. A process for preparing optically active hydroxy-, alkoxy-, amino-, alkyl-, aryl- or chlorine-substituted alcohols or hydroxy carboxylic acids having from 3 to 25 carbon atoms or their acid derivatives or cyclization products by hydrogenating the correspondingly substituted optically active mono- or dicarboxylic acids or their acid derivatives in the presence of a catalyst whose active component consists of
   rhenium or
   of rhenium and at least one further element having an atomic number of from 22 to 83, with the provisos that
   a. the at least one further element having an atomic number of from 22 to 83 is not ruthenium and
   b. in the case of the preparation of optically active 2-amino-, 2-chloro-, 2-hydroxy- and 2-alkoxy-1-alkanols by catalytically hydrogenating corresponding optically active 2-aminocarboxylic acids, 2-chlorocarboxylic acids, 2-hydroxycarboxylic acids and 2-alkoxycarboxylic acids or their acid derivatives, the at least one further element having an atomic number of from 22 to 83 is not palladium or platinum.

2. The process according to claim 1, wherein proviso b. is replaced by the proviso that the at least one further element having an atomic number of from 22 to 83 is not palladium or platinum.

3. The process according to claim 2, wherein the at least one further element having an atomic number of from 22 to 83 is selected from the group of the elements: Rh, Ir, Cu, Ag, Au, Co and Ni.

4. The process according to claim 3, wherein the at least one further element having an atomic number of from 22 to 83 is Rh or Ir.

5. The process according to claim 1, wherein optically active mono- or dicarboxylic acids or their acid derivatives are converted which have at least one stereocenter in the α- or β-position to at least one carboxylic acid function or acid derivative function derived therefrom to be hydrogenated.

6. The process according to claim 1 for preparing
   a. optically active 3-hydroxy-, 3-alkoxy-, 3-amino-, 3-alkyl-, 3-aryl- or 3-chloro-1-alkanols starting from the correspondingly substituted optically active 3-hydroxy-, 3-alkoxy-, 3-amino-, 3-alkyl-, 3-aryl- or 3-chloro-monocarboxylic acids or their acid derivatives or
   b. optically active hydroxy-, alkoxy-, amino-, alkyl-, aryl- or chlorine-substituted diols or triols or their cyclization products selected from the correspondingly substituted optically active dicarboxylic acids or their acid derivatives by hydrogenating both carboxylic acid functions or
   c. optically active alkyl- or aryl-substituted alkanols starting from the correspondingly substituted optically active alkyl- or aryl-substituted monocarboxylic acids
   in the presence of a catalyst whose active component comprises rhenium and palladium or rhenium and platinum.

7. The process according to claim 1, wherein the catalysts are used in supported form.

8. The process according to claim 7, wherein catalysts are used which, based in each case on the total weight of the finished catalyst and calculated as the metal, uses from 0.01 to 50% by weight of rhenium and from 0.01 to 30% by weight of the at least one further metal having an atomic number of from 22 to 83.

9. The process according to claim 7, wherein the support material used is $ZrO_2$, $TiO_2$, $Al_2O_3$, $SiO_2$, activated carbon, carbon blacks, graphites or high surface area graphite.

10. The process according to claim 9, wherein the rhenium and the at least one further element having an atomic number of from 22 to 83 is applied to the support in the presence of a reducing agent.

11. The process according to claim 1 for preparing 1,2-propanediol, 1,2-butanediol, 1,2-pentanediol, 1,3-pentanediol, leucinol, isoserinol, valinol, isoleucinol, serinol, threoninol, lysinol, phenylalaninol, tyrosinol, prolinol, 2-chloropropanol, 2-methyl-1-butanol, 1,2,4-butanetriol, 1,2,5-pentanetriol, 1,2,6-hexanetriol, 2,3-dimethylbutane-1,4-diol, 2-methylbutane-1,4-diol, 2-hydroxy-γ-butyrolactone, 3-hydroxy-γ-butyrolactone, 2-chloro-γ-butyrolactone, 3-chloro-γ-butyrolactone, 2-amino-γ-butyrolactone, 3-amino-γ-butyrolactone, 2-methyl-γ-butyrolactone, 3-methyl-γ-butyrolactone, 3-hydroxy-δ-valerolactone, 4-hydroxy-δ-valerolactone, 2-hydroxytetrahydrofuran, 2-methyltetrahydrofuran or 2-aminotetrahydrofuran.

12. The process according to claim 1, wherein the hydrogenation is carried out at a pressure of from 100 to 300 bar.

13. The process according to claim 1, wherein the hydrogenation is carried out at a temperature of from 30 to 180° C.

14. The process according to claim 1, wherein the hydrogenation is carried out in the presence of an acid.

15. The process according to claim 1, wherein the hydrogenation is carried out at a pressure of from 100 to 300 bar, at a temperature of from 30 to 180° C. and in the presence of an acid.

16. The process according to claim 4, wherein the hydrogenation is carried out at a pressure of from 100 to 300 bar, at a temperature of from 30 to 180° C. and in the presence of an acid.

17. A process for preparing optically active hyciroxy-, alkoxy-, amino-, alkyl-, aryl- or chlorine-substituted alcohols or hydroxy carboxylic acids having from 3 to 25 carbon atoms or their acid derivatives or cyclization products by hydrogenating the correspondingly substituted optically active mono- or dicarboxylic acids or their acid derivatives in the presence of a catalyst whose active component consists of rhenium or of rhenium and comprises at least one further element selected from the group of the elements: Pd, Pt, Rh, Ir, Cu, Ag, Au, Cr, Mo, W, Co and Ni, with the proviso that in the case of the preparation of optically active 2-amino-, 2-chloro-, 2-hydroxy- and 2-alkoxy-1-alkanols by catalytically hydrogenating corresponding optically active 2-aminocarboxylic acids, 2-chlorocarboxylic acids, 2-hydroxycarboxylic acids and 2-alkoxycarboxylic acids or their acid derivatives, the at least one further element is not palladium or platinum.

* * * * *